(12) United States Patent
Berberich et al.

(10) Patent No.: US 10,575,870 B2
(45) Date of Patent: Mar. 3, 2020

(54) SURGICAL INSTRUMENT SYSTEM

(75) Inventors: Sascha Berberich, Tuttlingen (DE); Sebastian Frey, Villingen-Schwennigen (DE); Michael Sauer, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 2677 days.

(21) Appl. No.: 11/971,536

(22) Filed: Jan. 9, 2008

(65) Prior Publication Data

US 2009/0018394 A1 Jan. 15, 2009

(30) Foreign Application Priority Data

Jul. 10, 2007 (DE) .................. 20 2007 009 713 U

(51) Int. Cl.
*A61B 1/00* (2006.01)
*A61B 17/34* (2006.01)

(52) U.S. Cl.
CPC ............................... *A61B 17/3417* (2013.01)

(58) Field of Classification Search
CPC ...................... A61B 1/018; A61B 1/00073
USPC ....... 600/104, 106, 114, 121, 124, 125, 105, 600/130, 135, 153, 155, 156, 160; 604/164.02, 524
See application file for complete search history.

(56) References Cited

U.S. PATENT DOCUMENTS

| | | | |
|---|---|---|---|
| 3,240,233 A | 3/1966 | Johnston | |
| 4,742,817 A * | 5/1988 | Kawashima et al. | 600/104 |
| 4,790,831 A * | 12/1988 | Skribiski | 604/524 |
| 4,951,977 A * | 8/1990 | Shutt | F16L 37/122 285/277 |
| 4,973,321 A * | 11/1990 | Michelson | A61B 1/00094 600/114 |
| 4,979,496 A * | 12/1990 | Komi | 600/113 |
| 4,991,565 A * | 2/1991 | Takahashi | A61B 1/00142 600/123 |
| 5,119,983 A | 6/1992 | Green et al. | |
| 5,575,756 A * | 11/1996 | Karasawa et al. | 600/157 |
| 5,681,342 A * | 10/1997 | Benchetrit | 606/192 |
| 5,800,342 A * | 9/1998 | Lee et al. | 600/114 |
| 6,142,931 A * | 11/2000 | Kaji | 600/114 |
| 6,471,678 B1 * | 10/2002 | Alvarez de Toledo | A61B 17/3478 600/104 |
| 6,827,710 B1 * | 12/2004 | Mooney et al. | 604/500 |
| 7,097,644 B2 * | 8/2006 | Long | 606/41 |

(Continued)

FOREIGN PATENT DOCUMENTS

DE 10022861 12/2001
DE 60114042 T 5/2006

OTHER PUBLICATIONS

Deutsches Patent—und Markenamt Search Report, 4 pages.

*Primary Examiner* — Alexandra L Newton
*Assistant Examiner* — Rynae Boler
(74) *Attorney, Agent, or Firm* — Whitmyer IP Group LLC

(57) ABSTRACT

The invention relates to a surgical instrument system, which comprises a hollow shaft as well as a shaft-type instrument that can be inserted into the hollow shaft. To create a surgical instrument system that consists of a hollow shaft and of a medical instrument that can be inserted into the hollow shaft and that is both simple in construction and capable of a range of uses, it is proposed according to the invention that at least one cam that reduces the inside diameter of the hollow shaft should be positioned on the interior of the hollow shaft.

10 Claims, 3 Drawing Sheets

(56) References Cited

U.S. PATENT DOCUMENTS

| | | | |
|---|---|---|---|
| 7,500,947 B2 * | 3/2009 | Kucklick et al. | 600/114 |
| 2006/0041186 A1 * | 2/2006 | Vancaillie | 600/128 |
| 2006/0149127 A1 * | 7/2006 | Seddiqui et al. | 600/104 |
| 2007/0043264 A1 * | 2/2007 | Gillis | A61B 1/303 |
| | | | 600/184 |
| 2009/0012362 A1 * | 1/2009 | Kucklick | A61B 1/317 |
| | | | 600/121 |
| 2009/0054728 A1 * | 2/2009 | Trusty | 600/114 |

* cited by examiner

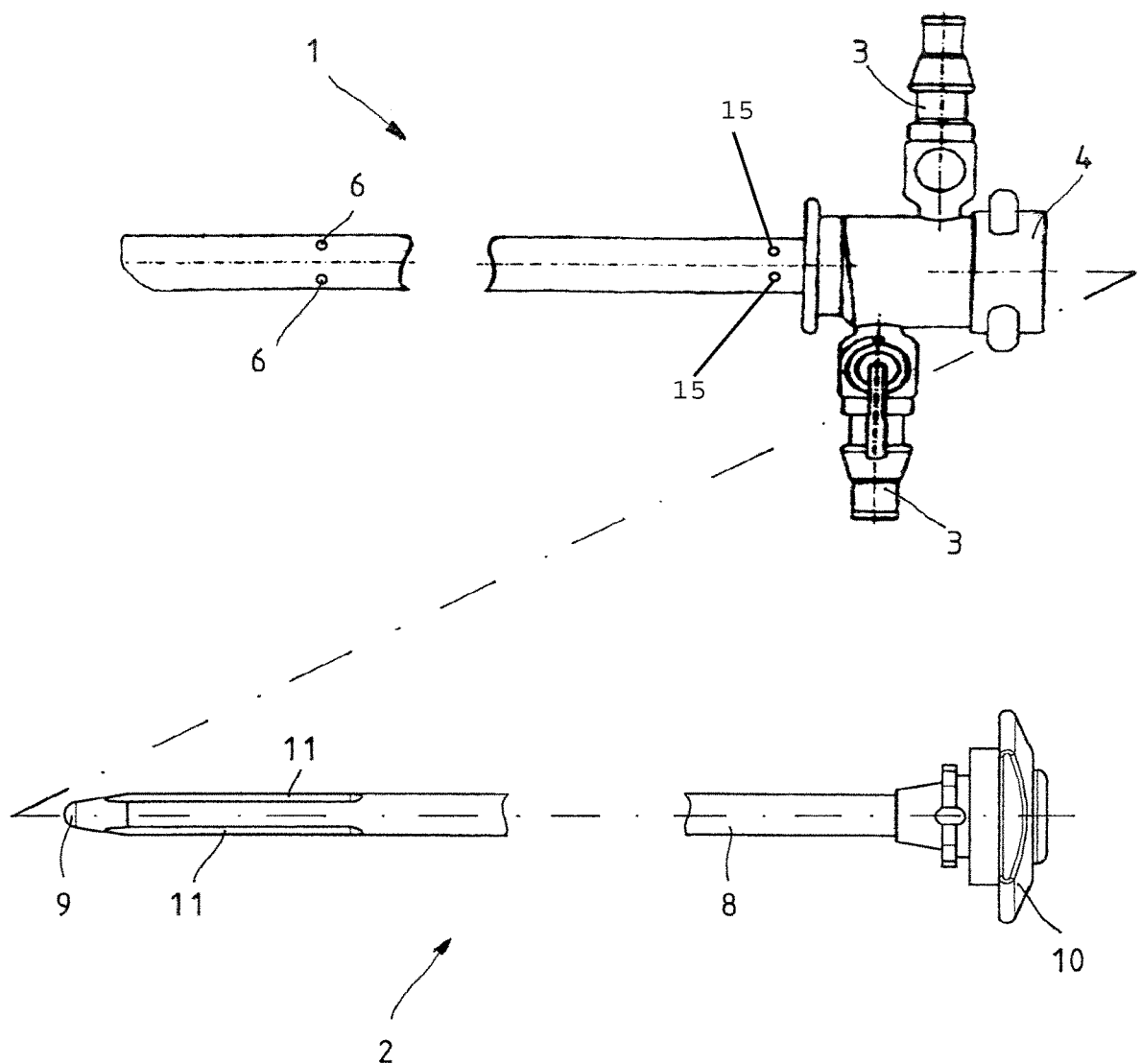

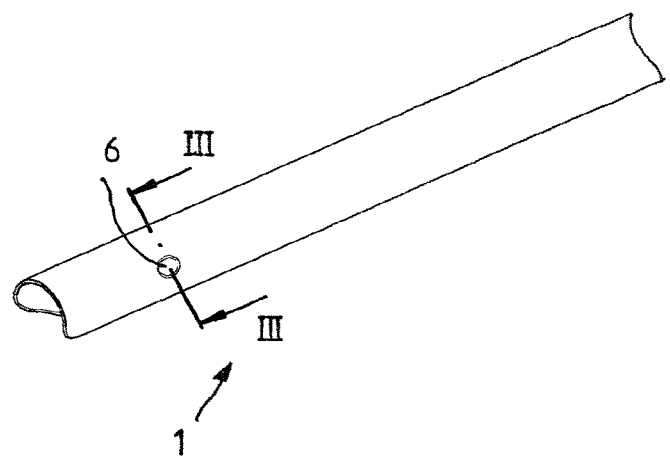
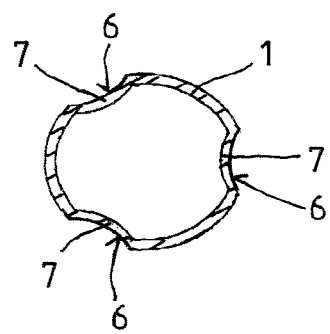
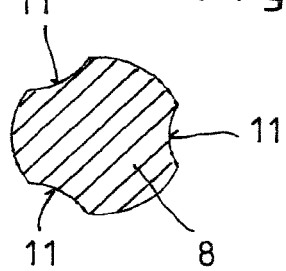
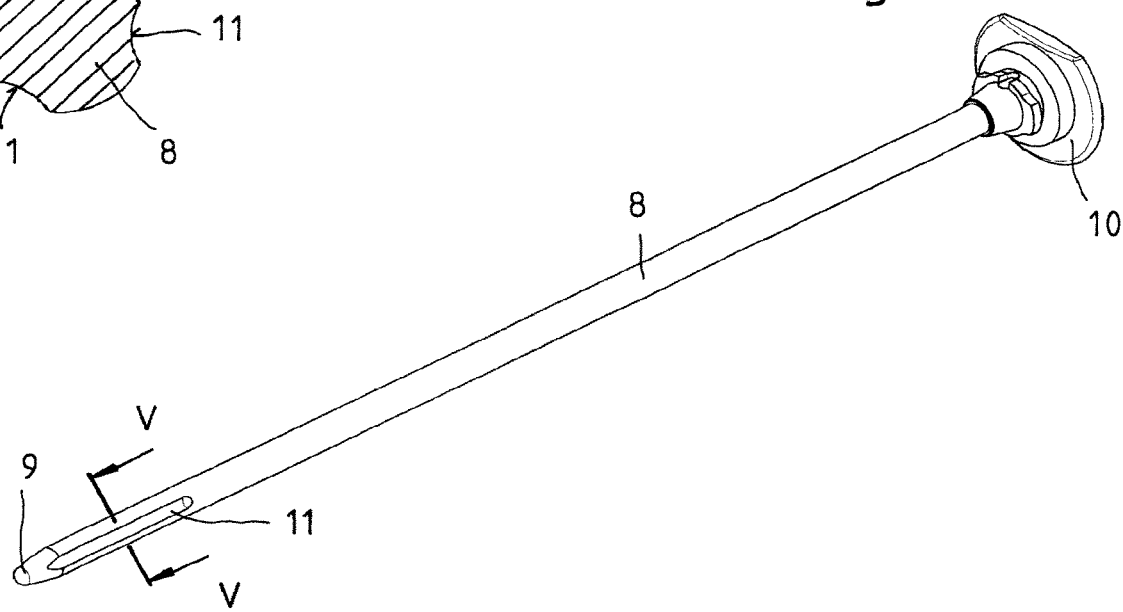

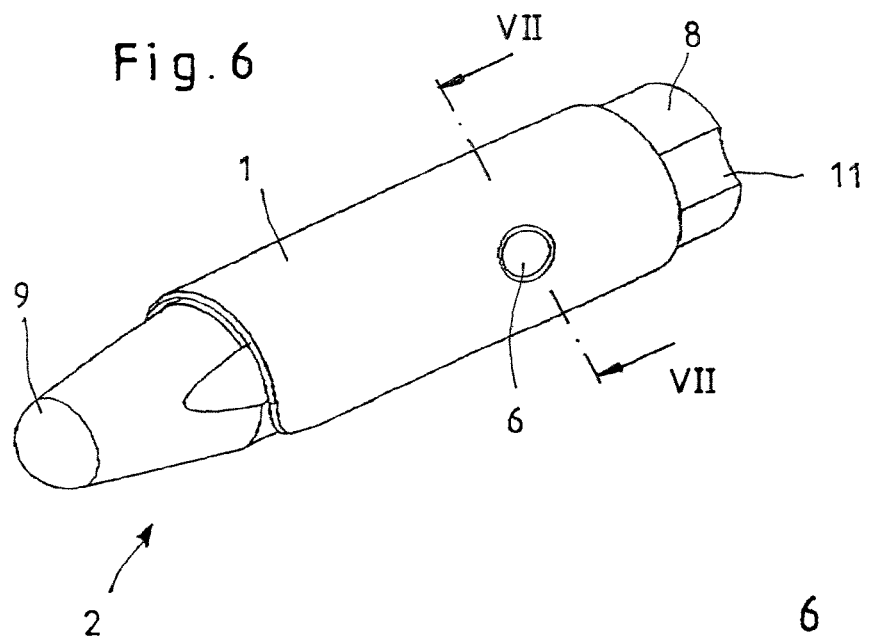
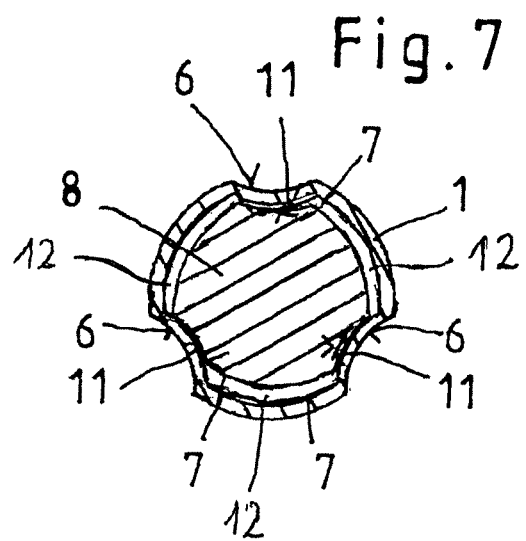
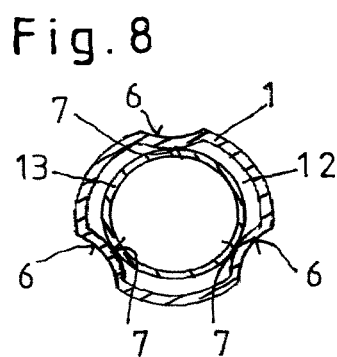

SURGICAL INSTRUMENT SYSTEM

CROSS-REFERENCE TO RELATED APPLICATIONS

The present application claims priority of German patent application No. 20 2007 009 713.1 filed on Jul. 10, 2007, the content of which is incorporated herein by reference.

FIELD OF THE INVENTION

The invention relates to a surgical instrument system, which comprises a hollow shaft as well as a shaft-type instrument that can be inserted into the hollow shaft.

BACKGROUND OF THE INVENTION

It is customary in endoscopic surgical interventions to create several means of access to the surgical area in order to have at least one accessway for conveying medical instruments such as cutting and/or gripping instruments into the surgical area for conducting an operation and to have at least one additional accessway for conveying an observation unit, such as an endoscope, into the area for observation and control of the operation.

The various medical instruments are conveyed into the operating area after configuration of an initial skin incision by hollow shafts. Because a great range of medical instruments are inserted into these hollow shafts, the shafts must be so configured that they fulfill the various requirements demanded of the shaft by the insertion of the particular instrument. For instance, while inserting an endoscope into the hollow shaft, in order to create sufficient space for rinsing inside the hollow shaft, by which the endoscope lens system can be cleaned during the operation, shafts known in the art comprise lateral rinsing holes or distal inserts, which on the other hand reduce the flow of rinsing agents and the turbulence or else are unnecessary or can even be a hindrance for other instrument inserts.

It is therefore the object of the invention to create a surgical instrument system that consists of a hollow shaft and of a medical instrument that can be inserted into the hollow shaft and that is of simple construction and offers a range of uses.

SUMMARY OF THE INVENTION

The invention fulfills this object in that on the interior of the hollow shaft at least one cam is positioned that reduces the inside diameter of the hollow shaft in such a way that a rinsing area is configured between the interior surrounding surface of the hollow shaft and the outer surrounding surface of the shaft-type instrument that can be inserted into the hollow shaft when the shaft-type instrument, such as an endoscope, comes into contact with its outer surrounding surface on the at least one cam.

The addition of individual cams on the interior wall of the hollow shaft has the advantage that these cams reduce the rinsing flow very little if at all.

It is proposed with a practical embodiment of the invention that several cams, preferably three, should be distributed over the inner surrounding surface of the hollow shaft. Providing several cams distributed over the surrounding surface makes possible a simple way of holding a medical instrument inserted in the hollow shaft, for instance an endoscope lens system, at a precise distance from the inside surrounding surface of the hollow shaft.

It is further proposed with the invention that the several cams should preferably be positioned in the area of the distal end of the hollow shaft and aligned in a circle, that is, that all cams should be arranged at an equal distance from the distal point of the hollow shaft.

To ensure that the rinsing flow is disturbed as little as possible by the cams extending into the hollow shaft, it is proposed with the invention that the cams should be configured as essentially point-shaped.

Contrary to what occurs in inserting medical instruments into the hollow shaft that happens to be already in the skin incision, when the hollow shaft is inserted into the skin incision by means of an expansion mandrel or obturator inserted into the hollow shaft, it is not desirable that a gap should be created between the inside surrounding surface of the hollow shaft and the outside surrounding surface of the shaft instrument inserted into the hollow shaft, because this could cause tissue damage by the sharp distal end of the hollow shaft.

In this type of application, in order to remove the distance-producing effect of the cams positioned on the inside wall of the hollow shaft, it is proposed with the invention that, in the shaft of the shaft-type instrument inserted into the hollow shaft, at least one recess should be configured corresponding with the at least one cam. The configuration of this recess has the effect that the corresponding cam can be inserted into this recess, while the rest of the instrument shaft can fill the inside diameter of the hollow shaft completely.

The cams of the hollow shaft that engage in the recesses of the instrument shaft, in addition, cause a rotation-proof blocking of the medical instrument inserted into the hollow shaft relative to the hollow shaft.

It is further proposed with the invention that with several cams positioned over the inside surrounding surface of the hollow shaft, the recesses corresponding with the cams in the shaft of the shaft-type instrument should be configured as grooves running in the axial direction of the shaft, such that the axial length of the grooves preferably corresponds to the position of the corresponding cams on the inside of the hollow shaft.

In order to allow that the medical shaft-type instrument that is to be inserted is inserted into the hollow shaft in a simple manner and in exact position and in the correct alignment with the hollow shaft, according to a preferred embodiment of the invention an additional cam is positioned on the inside of the hollow shaft in addition in the area of the proximal end, and in the shaft of the shaft-type instrument that is to be inserted into the hollow shaft, a recess is configured that corresponds with the additional cam and extends from the distal end of the shaft to the height of the additional cam.

This additional cam positioned in the area of the proximal end on the inside of the hollow shaft is preferably aligned in the axial direction flush with one of the other cams.

Finally it is proposed with the invention that the shaft-type instrument that can be inserted into the hollow shaft should be an obturator.

Further characteristics and advantages of the invention can be seen by means of the description of the appended illustrations, in which an embodiment of an inventive surgical instrument system is presented in exemplary form, without restricting the invention to this embodiment.

BRIEF DESCRIPTION OF THE DRAWINGS

FIG. 1 shows a schematic side view of an inventive surgical instrument system comprising a hollow shaft as well as a medical shaft-type instrument that can be inserted into the hollow shaft.

FIG. 2 shows a perspective view of a detail of the distal end of the hollow shaft.

FIG. 3 shows an enlarged section along the line III-III in FIG. 2.

FIG. 4 shows a perspective view of the medical instrument that can be inserted into the hollow shaft.

FIG. 5 shows an enlarged section along the line V-V of FIG. 4.

FIG. 6 shows a perspective view of a detail of the distal end of the hollow shaft with inserted medical instrument.

FIG. 7 shows a section along the line VII-VII of FIG. 6.

FIG. 8 shows a section according to FIG. 7 but with a different shaft-type instrument inserted into the hollow shaft.

DETAILED DESCRIPTION OF THE INVENTION

The surgical instrument system illustrated in FIG. 1 consists of an inventive surgical instrument system comprising a hollow shaft 1 as well as a medical shaft-type instrument 2 that can be inserted into the hollow shaft 1.

The hollow shaft 1 consists essentially of a hollow cylindrical tube on whose proximal end rinsing connections 3 and a coupling mechanism 4 for locked fixing of the medical shaft-type instrument 2 that is inserted into the hollow shaft 1 are positioned. In the illustrated embodiment of the hollow shaft 1, the distal end of the hollow shaft 1 comprises a return spring (Not Shown), but it is also possible of course to configure the distal end of the hollow shaft 1 in such a way that said end ends straight or has a distal end of a different shape or type.

As can be seen in particular from FIGS. 2 and 3, the hollow shaft 1 in the area of its distal end comprises three notches 6 that are distributed over the perimeter of the hollow shaft 1 and that configure point-shaped cams 7 that reduce the inside diameter of the hollow shaft 1 on the inside of the hollow shaft 1.

With the illustrated embodiment of the hollow shaft 1, the cams 7 are positioned in a circle at an equal distance from the distal end of the hollow shaft 1. It is also possible of course to arrange more or fewer cams 7 and cams 7 in other arrangements on the inside of the hollow shaft 1. In addition, the illustrated configuration of the cams 7 as point-shaped cams 7, which are formed by in-curving of the surrounding surface of the hollow shaft 1, constitutes only one possible means of designing and configuring the cams 7. What's essential is that the cams 7 in some sections reduce the inside diameter of the hollow shaft 1.

The shaft-type instrument 2 configured as a mandrel, for instance an obturator, consists, as can be seen from FIGS. 1, 4, and 5, essentially of a lengthwise extended shaft 8 whose distal end is configured as a rounded point 9 and on whose proximal end a handle 10 is positioned, which on the one hand facilitates the insertion and withdrawing of the shaft 8 into and out of the hollow shaft 1 and, on the other hand, constitutes a limiting stop for the insertion depth of the shaft 8 into the hollow shaft 1.

The handle 10, in addition, comprises appropriate catching instruments to secure the shaft-type instrument 2 on the coupling mechanism 4 of the hollow shaft 1.

As can be seen in particular from FIGS. 4 and 5, the shaft 8 of the shaft-type instrument 2 in the area of the distal end comprises three recesses 11 configured as grooves that are distributed over the perimeter of the shaft 8 and correspond with the cams 7 of the hollow shaft 1.

These grooves 11 serve, despite the cams 7 configured on the inside of the hollow shaft 1, to completely fill the hollow shaft 1 with the shaft 8 of the shaft-type instrument 2 that is to be inserted, when this is required. As shown in FIG. 7, the cams 7 engage with the grooves 11 and thereby allow an essentially fully flat lining of the hollow shaft 1 by the shaft 8 of the shaft-type instrument 2 inserted into the hollow shaft 1.

When it is required, however, that free space, for instance in the form of a rinsing area 12 (FIG. 8), should remain between the inner surrounding surface of the hollow shaft 1 and the outer surrounding surface of the shaft of the shaft-type instrument 2 that is to be inserted into the hollow shaft 1, these cams 7 configured on the inside of the hollow shaft 1, with a shaft 13 without recesses 11, for instance the shaft 13 of an endoscope lens system, produce this required distance because the shaft 13 with its surrounding surface is contiguous with the cams 7 and thus is held at a distance from the inside wall of the hollow shaft 1.

Alternatively to the previously described configuration of the rinsing area 12 on a shaft without recesses 11, it is also possible to configured the rinsing area 12 in that the depth of the recesses/grooves in the shaft 8 or 13 of the shaft-type instrument 2 is less than the height of the cams 7, so that the width of the rinsing area 12 can be determined by the depth of the recesses/grooves 11.

The sectional view in FIG. 8 shows a division of the rinsing area 12 into three rinsing channels. It should be pointed out that these rinsing channels are configured only in the immediate contact vicinity of the shaft 3 on the cams 7, but before and behind the cams 7 the rinsing area takes up the entire perimeter surface between the inside surrounding surface of the hollow shaft 1 and the outer surrounding surface of the shaft 13 of the shaft-type instrument that is to be inserted into the hollow shaft 1.

The previously described surgical instrument system is used as follows.

In a first operational step, for instance by means of a sharp trocar mandrel, at least one skin incision is produced by which thereafter the medical instruments required for the endoscopic operation can be conveyed to the operating area.

The medical instruments are inserted through the skin incision into the operating area by means of sleeves, such as the hollow shaft 1, inserted into the skin incision.

Because the operationally produced cut of the skin incision is to be kept as small as possible, but thereafter medical instruments with a larger diameter must also be inserted into the operating area, it is necessary thereafter, after configuring the skin incision, to widen the skin incision by using the tissue elasticity.

The widening can, for instance, be carried out by means of the shaft-type instrument 2, which is pushed with its rounded point 9 forward into the skin incision and widens said incision with the conical shape of the point 9 upon further insertion of the shaft 8. To be able to insert the hollow shaft 1 into the skin incision simultaneously with the widening of the skin incision, first the shaft-type instrument 2 is inserted into the hollow shaft until the cams 7 of the hollow shaft 1 engage in the recesses/grooves 1 of the shaft 8.

In this combination depicted in FIG. 6, the instrument system is inserted into the skin incision. To avoid injuries of the tissue upon insertion of the hollow shaft into the skin incision by the sharp distal end edge of the hollow shaft 1, it is urgently necessary in this stage of the operation that the shaft 8 of the shaft-type instrument 2 inserted into the hollow shaft 1 completely fills up the hollow shaft 1, in particular at the distal end, in order thereby to ensure seamless transition from the outer diameter of the shaft 8 to the outer diameter of the hollow shaft 1.

After placing the hollow shaft 1 in the skin incision, the shaft-type instrument 2 in the form of an expansion mandrel can be withdrawn again from the hollow shaft 1.

The hollow shaft henceforth forms a free accessway to the operating area, through which further medical instruments can be inserted into the operating area.

Upon inserting an endoscope lens system into the operating area, to ensure a constantly clear field of vision it is necessary to rinse the lens system. As can be seen from FIG. 8, said necessary rinsing area 12 is produced inside the hollow shaft 1 in that the shaft 13 of the endoscope lens system has no recesses/grooves, so that the shaft 13 with its surrounding surface is contiguous with the cams 7 and thus is held at a distance from the inside wall of the hollow shaft 1 while forming the rinsing area 12.

To be able to insert the insertable medical shaft-type instrument 2 into the hollow shaft 1 in simple manner and in the correct alignment to the hollow shaft 1, an additional cam 7 corresponding to notches 15 of FIG. 1 can be positioned on the inside of the hollow shaft 1 in addition in the area of the proximal end, and in the shaft 8 of the shaft-type instrument 2 that is to be inserted into the hollow shaft 1 a recess 11 can be configured that corresponds with the additional cam 7 and extends from the distal end of the shaft 8 to the additional cam 7.

The surgical instrument system of this configuration is characterized in that it ensures both a range of possible uses and a constantly high degree of operating safety and ease of operation.

What is claimed is:

1. A surgical instrument system comprising a hollow shaft with an open distal end as well as a medical shaft-type instrument that is insertable into the hollow shaft and withdrawable completely out of the hollow shaft via an open proximal end of the hollow shaft, whereby the hollow shaft is configured as a hollow cylindrical tube which coaxially surrounds the shaft-type instrument about a whole circumference and whereby on an interior surface of the hollow shaft several projections are configured that reduce an interior diameter of the hollow shaft,
   characterized in that the projections are configured as discrete point-shaped protrusions, each point-shaped protrusion is aligned with a cross-section of the hollow shaft that is perpendicular to a longitudinal axis of the hollow shaft in such a way that each point-shaped protrusion forms a point-shaped contact point with an outer surface of the shaft-type instrument when inserted into the hollow shaft, and each point-shaped protrusion reduces the interior diameter of the hollow shaft in such a way that a rinsing area is configured between the interior surface of the hollow shaft and the outer surface of the shaft-type instrument, and
   characterized in that several grooves running in a longitudinal direction of a shaft of the shaft-type instrument are configured in the shaft of the shaft-type instrument, wherein said grooves correspond with the point-shaped protrusions of the hollow shaft to provide a rotation-proof blocking of the shaft of the shaft-type instrument relative to the hollow shaft, wherein the depth of the grooves in the shaft of the shaft-type instrument is less than the height of the point-shaped protrusions, so that the rinsing area is configured between the interior surface of the hollow shaft and the outer surface of the shaft-type instrument, and wherein the axial length of the grooves corresponds to the position of the corresponding point-shaped protrusions on the interior surface of the hollow shaft.

2. The surgical instrument system according to claim 1, characterized in that the several projections are distributed over the interior surface of the hollow shaft.

3. The surgical instrument system according to claim 2, characterized in that the several projections are positioned in a circle.

4. The surgical instrument system according to claim 1, characterized in that at least one of the projections is positioned in an area of the distal end of the hollow shaft.

5. The surgical instrument system according to claim 1, characterized in that on the interior surface of the hollow shaft an additional projection is positioned in an area of the proximal end of the hollow shaft, and that in the shaft of the shaft-type instrument that is to be inserted into the hollow shaft, a recess is configured that corresponds with the additional projection and extends from a distal end of the shaft of the shaft-type instrument to the position of the additional projection on the interior surface of the hollow shaft when the shaft-type instrument is inserted into the hollow shaft.

6. The surgical instrument system according to claim 5, characterized in that the additional projection positioned in the area of the proximal end on the interior surface of the hollow shaft is aligned in an axial direction flush with one of the other projections.

7. The surgical instrument system according to claim 1, characterized in that the shaft-type instrument that can be inserted into the hollow shaft is an endoscope.

8. The surgical instrument system according to claim 1, characterized in that the shaft-type instrument that can be inserted into the hollow shaft is an obturator.

9. The surgical instrument system according to claim 2, characterized in that three projections are distributed over the inner surface of the hollow shaft.

10. A surgical instrument system comprising:
   a hollow shaft with an open distal end and an open proximal end;
   a first shaft-type instrument and a second shaft-type instrument, the first and second shaft-type instruments are configured to be separately inserted into and withdrawn out of the hollow shaft via the proximal end of the hollow shaft;
   the hollow shaft being configured to coaxially surround one at a time one of the first shaft-type instrument or the second shaft-type instrument, a distal half of the hollow shaft having a plurality of discrete point-shaped protrusions extending inwardly from an inner surface of the hollow shaft, all point-shaped protrusions being positioned along a single transverse plane that is perpendicular to a longitudinal axis of the hollow shaft,
   the first shaft-type instrument having a first shaft with a plurality of grooves that are disposed in an outer surface of the first shaft and that extend in a longitudinal direction of the first shaft, wherein said grooves are configured to engage the point-shaped protrusions of the hollow shaft to occlude the hollow shaft and to provide a rotation-proof blocking of the first shaft relative to the hollow shaft when the first shaft-type instrument is inserted into the hollow shaft;
   the second shaft-type instrument having a second shaft with an outer surface, a perimeter of the second shaft being configured so that the outer surface of the second shaft contacts an apex of each point-shaped protrusion and so that a rinsing area is provided between the inner surface of the hollow shaft and the outer surface of the second shaft when the second shaft-type instrument is inserted into the hollow shaft.

* * * * *